United States Patent [19]

Borras et al.

[11] Patent Number: 4,973,308
[45] Date of Patent: Nov. 27, 1990

[54] INJECTION SYRINGE WITH MECHANISM PREVENTING REUSE

[75] Inventors: Ramón C. Borras; Ramón M. Rovira, both of c/Juan XXIII n. 15-19, Barcelona, Spain, 08950

[73] Assignees: Ramón M. Rovira; Thermacrome de España S.A.; Ramón C. Borras, all of Barcelona, Spain; part interest to each

[21] Appl. No.: 194,970

[22] Filed: May 17, 1988

[30] Foreign Application Priority Data

May 22, 1987 [ES] Spain ................................. 8701507
Dec. 9, 1987 [ES] Spain ................................. 8703522

[51] Int. Cl.⁵ .............................................. A61M 5/18
[52] U.S. Cl. ...................................... 604/110; 604/228
[58] Field of Search ............... 604/110, 187, 218, 228, 604/229, 231

[56] References Cited

U.S. PATENT DOCUMENTS

| 3,951,146 | 4/1976 | Chiquiar-Arias | 604/110 |
| 4,233,975 | 11/1980 | Yerman | 604/110 |
| 4,687,467 | 8/1987 | Cygielski | 604/110 |
| 4,731,068 | 3/1988 | Hesse | 604/110 |
| 4,747,829 | 5/1988 | Jacob et al. | 604/110 |
| 4,775,363 | 10/1988 | Sandsdalen | 604/110 |
| 4,775,364 | 10/1988 | Alles | 604/110 |
| 4,781,684 | 11/1988 | Trenner | 604/110 |
| 4,863,427 | 9/1989 | Cocchi | 604/110 |
| 4,874,372 | 10/1989 | McArthur et al. | 604/110 |
| 4,915,692 | 4/1990 | Verlier | 604/110 |
| 4,923,443 | 5/1990 | Greenwood et al. | 604/110 |

FOREIGN PATENT DOCUMENTS

| 304386 | 2/1989 | European Pat. Off. | 604/110 |
| 321414 | 6/1989 | European Pat. Off. | 604/110 |
| 2298340 | 1/1975 | France . | |
| 8906146 | 7/1989 | PCT Int'l Appl. | 604/110 |
| 531282 | 4/1984 | Spain . | |
| 2015883 | 3/1979 | United Kingdom . | |

Primary Examiner—Stephen C. Pellegrino
Assistant Examiner—Ralph Lewis
Attorney, Agent, or Firm—Fleit, Jacobson, Cohn, Price Holman & Stern

[57] ABSTRACT

Disposable syringe for injecting fluids having a tubular body (1), a working stem (5) coupled to a piston (4), with a clearance between them, whereby movements of stem (5) determine relative corresponding displacements, of a determined length, between stem (5) and piston (4). A built-in tubular auxiliary element (8) is attached to the piston (4) and stem (5) by a sliding friction toothed attachment, which, depending on such relative displacements, advances within the syringe in uniform increments unidirectionally. Predetermined displacement of element (8) causes the syringe to become unserviceable. Built-in configurations (9), (13) and (14) prevent movement between the stem and piston as well as withdrawing of these elements from the body (1) until use of the syringe.

9 Claims, 4 Drawing Sheets

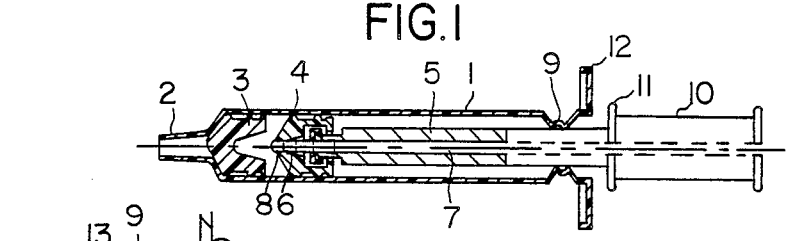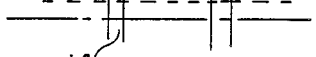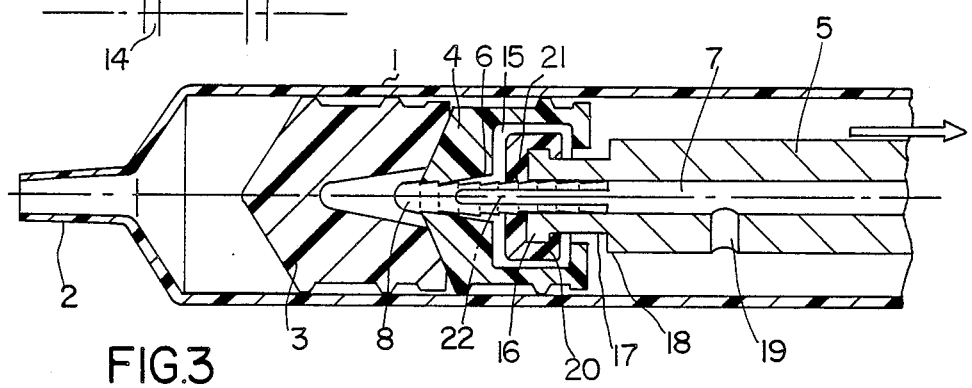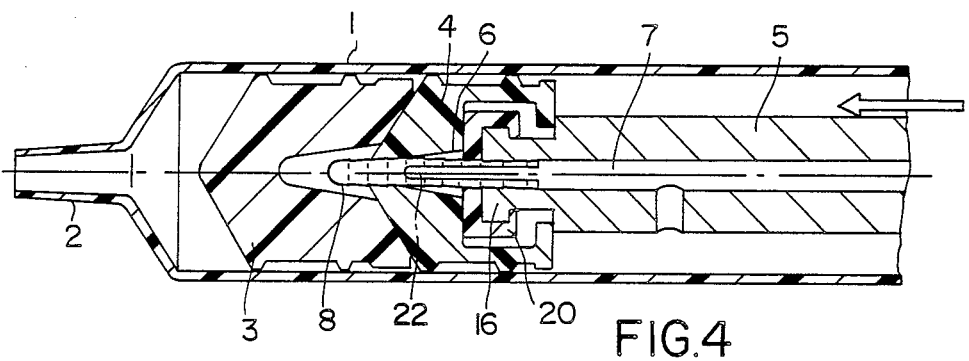

INJECTION SYRINGE WITH MECHANISM PREVENTING REUSE

BACKGROUND OF THE INVENTION

This invention relates to a disposable syringe for injecting fluids, and more particularly to a syringe having a device as a part there of which makes the syringe unserviceable once it has been used, and therefore assures that it is disposed of and not reused, and thus is specially designed to reduce the risk of transmission of infectious illness.

The syringe of this invention is in its general structure, fully equivalent to those presently in use; it shall be presented according to standards, in sterile packages, and, due to its special constitutive features compelling only a single use, it guarantees utilization, in any case, with the highest sanitation conditions.

In addition, this syringe has a production cost similar to that of conventional syringes, as it incorporates only one or two additional pieces, depending on the particular embodiment, which are easy to obtain.

Syringes are known that have built-in deposit, or deposits, containing products to apply though such syringes because of their structure, cost and operation, are completely different from the invention. Examples of such syringes are shown in U.S. Pat. No. 3,941,128, Australian Patent No. 16,859, Spanish Patent No. 531,282 and French Patent No. 2,298,340. However this syringe in order to be made unserviceable depends on voluntary action by the user.

BRIEF SUMMARY OF THE INVENTION

The object of the invention is to provide a syringe having an elongated hollow tubular body finished at one end by a duct adapted to receive a hollow needle connected to the inside of the duct, the tubular body having a biased end, and having in its interior a slidably mounted piston, tightly fitted and attached to a working stem. Up to this point the matter described is a fully conventional structure with component parts, wherein an end portion of the working stem is interlocked with a solid body portion by an attachment that provides bidirectional movement, of a confined length, of such end portion of the stem, with respect to the stem, or solid body portion corresponding to the movement of the working stem.

The syringe of the invention is characterized in addition by integrating an auxiliary element slidably mounted in the tubular body and associated by its two ends with specific friction or gearing attachments to the piston and working stem end. To achieve this, differentiated means are provided for retaining and passing the auxiliary element through a piston and the end portion of the stem which, due to the clearance between the stem and piston when operating the syringe, thereby subject these parts to some stresses determining related linear displacements for advancing the auxiliary element in a single direction. This auxiliary element adopts a configuration which is auxiliary to the unidirectionality and length of its incremental displacements within the tubular body.

The unit formed by the working stem, piston and auxiliary element, constitutes a device which makes it possible to activate different actuators to make the syringe become unserviceable after a number of preestablished sequences. Thus, for example, after a number of programmed predetermined displacements in two opposite directions, consecutively, of the working stem, in the conventional operation of the syringe, the auxiliary element is displaced to a point producing unserviceability of the aspiration function of the syringe, or preventing the drive of the stem on the piston.

The syringe body has some built-in means, such as a locking configuration, to avoid relative accidental movement between the working stem and the piston until the moment of using the syringe. Also, a configuration of the mouthpiece, or of another part of the syringe, is provided that prevents withdrawal of the piston and/or working stem from inside the tubular body.

BRIEF DESCRIPTION OF THE DRAWINGS

A detailed description of the invention is given below with reference to the accompanying drawings showing some preferred embodiments, which are to be understood only as illustrative and non-limiting, examples wherein:

FIG. 1 is a longitudinal cross-sectional view of an embodiment of the syringe according to this invention;

FIG. 2 is an enlarged detail of part of FIG. 1 showing the working stem locking with the wall of the tubular body of the syringe until the moment of using the syringe;

FIGS. 3 to 6 are enlarged views of a part of FIG. 1 showing the invention in different operative positions including the moment its unserviceability occurs;

DETAILED DESCRIPTION

Figure 5:
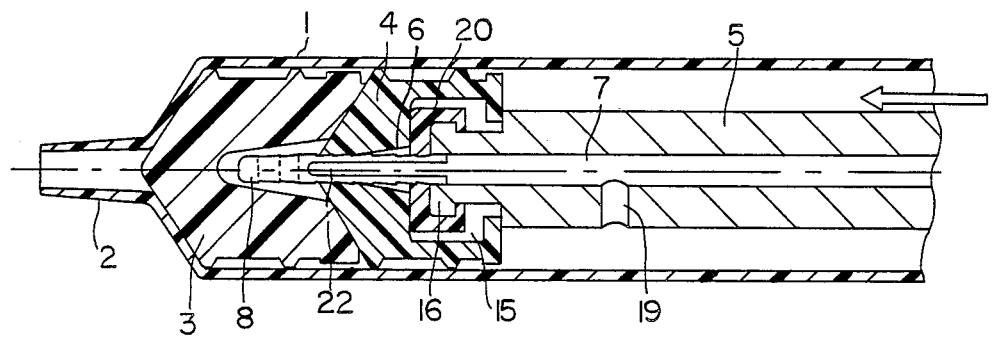

Referring to FIG. 1, the syringe of the invention has a tubular body or cylinder 1, finished at one of its ends by a duct or nozzle 2 adapted to receive by connection thereto a conventional hollow needle, not shown. Inside body 1, is a first loose piston 3 and a second piston 4 attached to working stem or drive piston rod 5, the two elements 4, 5 having ducts 6, 7, respectively, aligned along the axis of body 1, in which are respectively introduced, with frictional attachment, the ends of an auxiliary element 8, element 8 being slidably mounted in elements 4, 5 for advancing therethrough in a single direction in uniform increments. In FIG. 1 it is observed that near the mouthpiece of the tubular body 1 is a throttle 9, or annular reduced diameter section (FIG. 2) made after assembly inside body 1 of elements 4, 5 and 8, and produced for example by a thermal forming operation, where tubular body is made of a fitted thermoplastic material.

In addition FIG. 1 shows handle 10 of working stem 5 having an annular rib 11 that functions as a stop for limiting advance of stem 5 when it engages a flange 12, for example, on the mouthpiece of the syringe, according to a conventional configuration and to ease handling of the syringe In FIG. 2, we can see that in the internal face of throttled area 9 of tubular body 1 an annular offset 13 is provided corresponding positionally to a coaxial rib 14 on working stem 5 constituting a tongue and groove configuration, for interlocking, that prevents accidental displacements between stem 5 and piston 4, before using the syringe. When intentionally drawing on stem 5 by handle 10 such locking means are uncoupled, for which purpose both elements are made of resilient materials.

FIG. 3 shows in larger detail that inside piston 4 a cavity 15 is defined wherein is housed and retained a larger end 16, of stem 5. The configuration of the stem 5 end portion includes a length of reduced diameter section 17 attached to straight step 18 which determines that all the inner and outer movements of stem 5 displace its larger end 16 an equivalent distance inside cavity 15 and relative to piston 4, such distance being confined by the length of smaller section 17, and/or the span of the cavity 15, before stem 5 drives or pushes piston 4.

FIG. 3 also shows axial duct 7 in stem 5 with an outlet 19, for atmospheric intake and also cap 20 of resilient material coupled to and covering larger end 16 of stem 5. This cap 20 has a passage hole 21 that remains facing duct 7 and through which is arranged tubular auxiliary element 8 having its external face stepped by a plurality of adjacent frustoconically shaped sectors, and having a linear groove 22 extending part way along its length from one of its ends. The other end of element 8 is inserted into the frustoconically shaped part and the adjoining cylindrical part of hole 21 where element 8 establishes an adjustable but tight fitting engagement. Piston 4 is made of a resilient material with operating conditions different from those of cap 20. Due to the orientation of the frustoconically shaped steps of auxiliary element 8 as shown in FIG. 3, which shows the first stage of the operation of the syringe. In this position element 8 has sealed the interior of piston 3 and tube 1 from the atmosphere so that retracting movement of piston 4 retracts piston 3 with it by creating a vacuum in chamber 23 and between the pistons. When working piston 5 is retracted auxiliary element 8 remains fixed by greater friction attachment in the cylindrical end section of duct 6, while cap 20, made of material resiliently weaker than piston 4, together with end 16 of stem 5 is retracted relatively to piston 4 and auxiliary element 8, passing over a step of this element.

A further inward movement of stem 5 will advance auxiliary element 8, in the duct 6, as shown in FIG. 4, because element 8 cannot go backwards through hole 21 of cap 20 since the latter is supported against larger portion 16 of stem 5 and the stepped configuration of element 8 prevents it.

In this way, each consecutive forward and backward movement of working piston 5 corresponds to one step incremental movement of auxiliary element 8 for advancing element 8 along piston 4.

Figure 6:
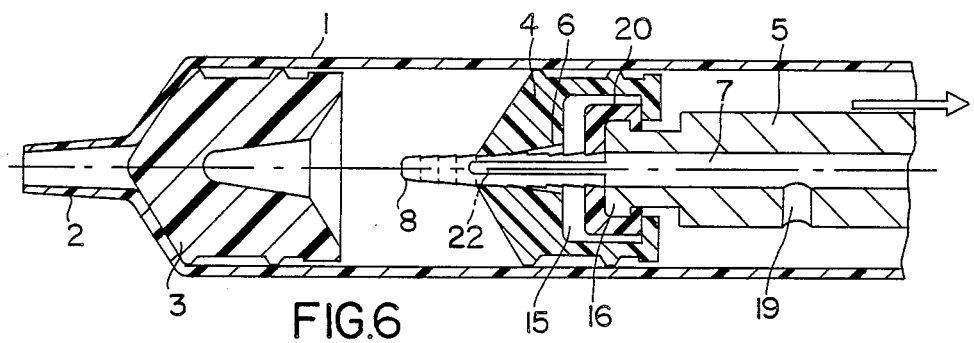

When groove 22 of auxiliary element 8 reaches the inner end of duct 6 of piston 4, as shown in FIG. 5, groove 22 allows communication with the atmosphere, through its passage and through the ducts 7 and 19, of the space enclosed between pistons 3 and 4. Thus, as shown in FIG. 6, piston 3 cannot be further operated backwardly, the loose piston 3 remains, and the suction function of the syringe becomes unserviceable.

Figure 7:
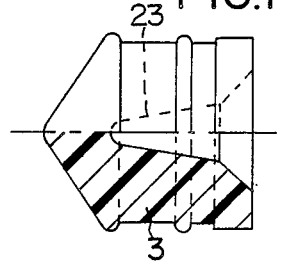
FIG. 7 is a partial cross-sectional view of one of two pistons used in the syringe of the invention.
Figure 8:
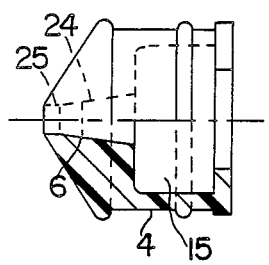
FIG. 8 is a view similar to FIG. 7 showing the other of the two pistons.

FIGS. 7 and 8 show the pistons 3 and 4, the former having a cavity 23 to allow the displacement therein of auxiliary element 8. In piston 4 large cavity 15 communicates through duct 6 with the inner end of piston 4, duct 6 having a frustoconically shaped portion 24 ending in cylindrical section 25 in order to establish a tight adjustment facility on element 8 and provide a moderated frictional engagement therewith.

The operation of the disclosed syringe will be possible using a single piston, although in such case, when the auxiliary element 8 communicates the interior enclosure between tubular body 1 and piston 4 with the atmosphere, the syringe becomes unserviceable and if one tries to push on the piston, the liquid in front of it will pass to the other side of the piston, whereby effective injection becomes impossible.

Within the capabilities of this invention, is an arrangement of referred elements where the auxiliary element instead of advancing towards the end of the syringe where the needle is coupled, advances, step by step, as explained, but in the opposite direction. In this latter case, should the syringe integrate a single piston, the auxiliary element 8, whenever visible by protruding beyond the piston, would provide the user with a visible indication that the syringe is still operative, while when disappearing inside the piston, it will clearly show that the stages this syringe provides are finished.

The form of the auxiliary element 8 is also to be considered as accessory, as well as the passage 19 for atmospheric intake, because considering that element 8 will advance in the opposite direction as explained, it could act as a simple tap establishing communication with the atmosphere of the enclosed area at the inner end of piston 4, once it is no longer supported at its end on the cylindrical section 25 of the duct 6, by means of duct 6 and a passage established through the annular wall of the cavity 15 in piston 4, for example.

The auxiliary element 8 must be located in every case, at the initial mounting position of this syringe, in an exact position, relative to piston 4 and stem 5, inserting it through duct 7 or duct 6, depending on its forward direction of advancement with the assistance of a gage-pusher (not-shown).

Figure 9:
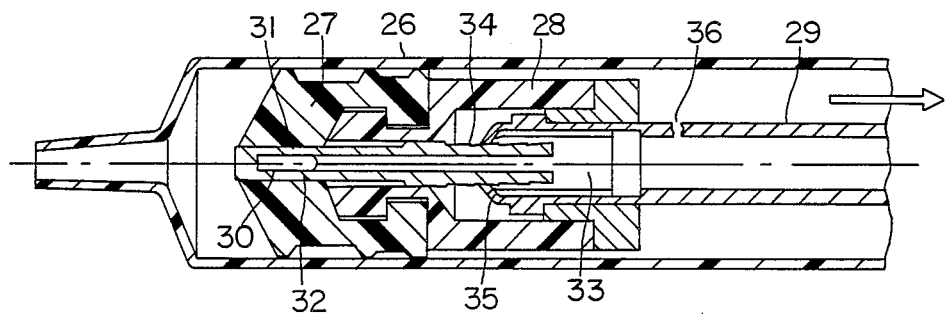
FIG. 9 is a view similar to FIG. 3 showing a further embodiment of the syringe of the invention in which the working stem remains attached to a rigid body which in turn is coupled to the piston and showing as well an alternative configuration of the auxiliary element and its fastening means.

FIG. 9 shows a syringe whose body 26 houses a single piston 27 slidably mounted in the inside, and attached to a hollowed out part 28, which has coupled in its inside the larger end of working stem 29. Associated by its ends to stem 29 and piston 27 is auxiliary element 30, constituted by a tube closed at one of its ends having a part housed, with frictional attachment, in a aisle 31 of piston 27 and having in its area remote from its closed end, one or several holes 32 that remain sealed during part of the lengthwise displacement of auxiliary element 30. The other end of element 30 remains housed in a tubular duct member 33 arranged at the end portion of stem 29 and has a stepped external configuration 34 in the form of frustoconical sections, which is engaged by a resilient clamping means in the form of pins or projections 35 embracing it, provided at the end of duct member 33. A gearing/frictional attachment is thereby obtained whereby retraction of stem 29 causes the clamping means to slip over one frustoconical section and inward movement engages the clamping means on element 30 to push it inwardly. The stem 29 has an aperture 36 for atmospheric intake.

Figure 10:
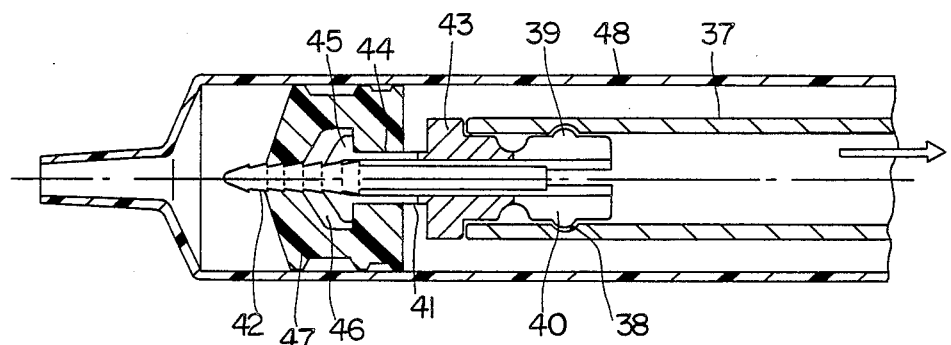
FIGS. 10 and 11 are views similar to FIG. 9 showing a different embodiment of the syringe of the invention in which the displacement of the auxiliary element produces separation between the working stem and piston.
Figure 11:
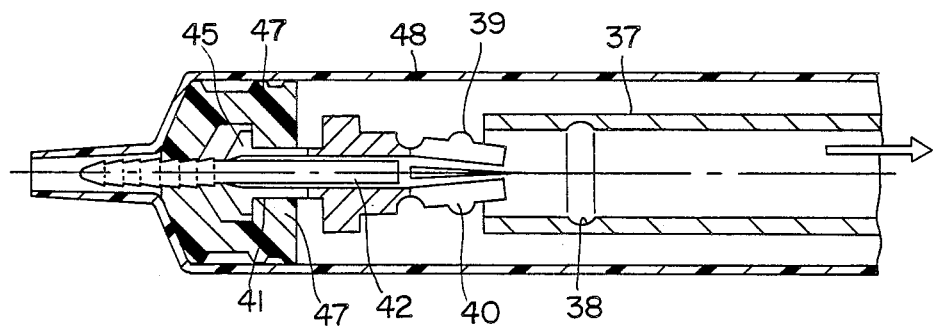

FIGS. 10 and 11 show an embodiment of the syringe where the working stem 37, in the form of a tube, has in the internal wall of an area near to its internal end an annular groove 38 where a rib ring profile 39 is coupled, rib 39 protruding from a single part 40 inserted in tube 37, and expanded by introducing through it a plane rod type section of an auxiliary element 41, the distal portion 42 of element 41 having an outer stepped wall that passes through piston 47. Expandable part 40, is continued by a double cylindrical portion 43 which is extended in turn by a reduced tubular throat section 44, ending in radial pins 45. Parts 44 and 45 remain retained inside the hollow interior 46 of piston 47, slidably mounted inside body 48 of the syringe allowing the displacement in two opposite directions of end portions 44, 45 of working piston 37.

In this embodiment, after a number of displacements of the working piston 37, the auxiliary element 41 has advanced through piston 47 and part 40 an leaves the inside of part 40, which thereafter not being expanded by element 41, releases rib ring 37 from groove 38 and thereby the working piston 37 from its association with the piston 47 as illustrated in FIG. 11.

Figure 12:
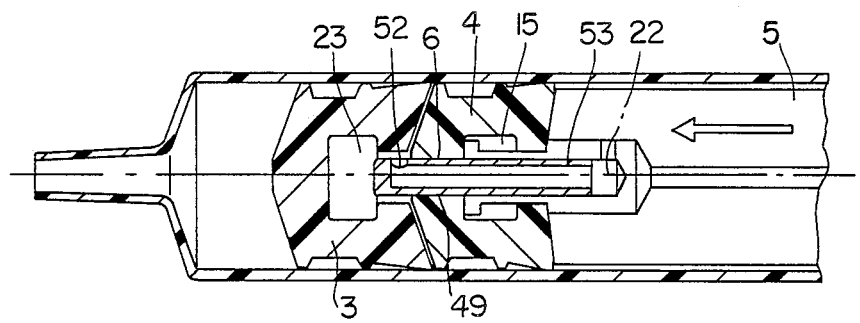
FIGS. 12 and 13 are views similar to FIG. 9 which show two further embodiments of the syringe of the invention characterized by forms of the auxiliary element adapted for retaining on the working stem.
Figure 13:
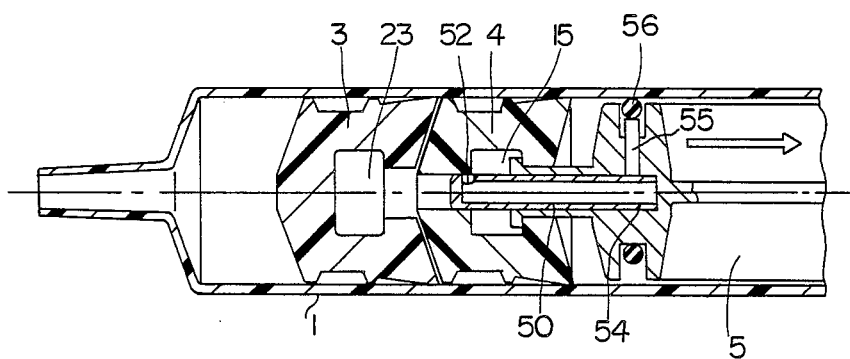
Figure 14:
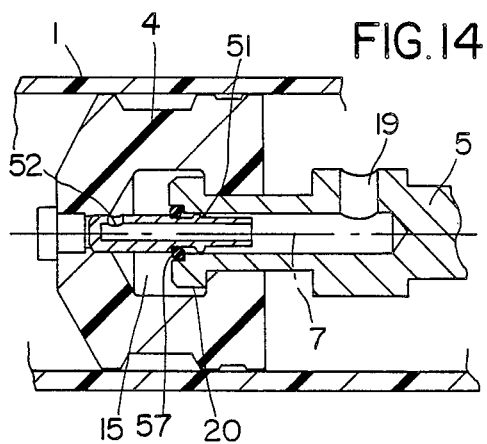
FIG. 14 is an enlarged detail of a further embodiment characterized by a certain configuration of the auxiliary element and attachment means at the working stem end.

FIGS. 12, 13 and 14 show some variants equivalent to the syringe of FIGS. 1 to 6, where only the form of the auxiliary element has been modified, marked in these figures by numerals 49, 50 and 51, as well as retaining means of such element, at the end of the working piston. For simplification parts numbers common to the other figures have been used.

In FIG. 12, the auxiliary element 49 is formed by a plain tube with a hole 52, with the end inserted in duct 6 of the piston 4, and its other end arranged inside a housing 53 of the end of stem 5 that has an outlet 22 for atmospheric intake.

The FIG. 13 embodiment is similar to that of FIG. 12, but the end 54 of the auxiliary element 50 is retained in the end portion of stem 5 by a pin 55, urged radially by resilient washer 56.

Finally, FIG. 14 introduces the variant of fastening the auxiliary element 51, of plain tubular configuration, at the end of stem 5 by means of an O-ring 57.

It is clear by all the disclosed embodiments herein, up to this point, that the essential features of the invention resides in a particular coupling between the working stem and the piston, which always produces a relative movement of the stem with respect to the piston, prior to displacement of the piston when operating the syringe. The auxiliary element advances in a single direction and engages by its two ends, by means of a differentiated working attachment, to the piston and stem. Because of the displacement of the auxiliary element, by its simplicity and effectiveness communication with the atmosphere of the interior area at the inner end of the piston is obtained to render the syringe unserviceable, and in suction function, although some other performances could be carried out, with results more or less equivalent, which must therefore be considered included in the invention.

Also means used to lock the working stem relative to the piston until starting the operation of the syringe are to be considered accessory, because though a tongue-groove configuration has been described for interlocking, many other industrially workable solutions are feasible, for example attaching the piston to the body of the syringe by a plastic microwelding, arranging a tap or fixing device at the end of the stem, etc.

As for means to prevent the stem and piston withdrawal, once installed in the syringe, although a throttle has been proposed in the mouthpiece area because of its simplicity, many other known solutions can be used with similar results and thus the one described is not to be understood as limitative.

For greatest security, material will be used to constitute the body of the syringe having properties capable of sustaining breakage or sawing stresses for the use intended.

Having disclosed the invention in this application in a sufficient manner in order that the essential features thereof are understood by a technician skilled in the art, the invention includes variations of detail not altering its features, such as different configurations of the stem 5, pistons 3, 4, auxiliary element 8, resilient element 20, locking means 13-14 and retaining means 9, fulfilling functions equivalent to that disclosed, the basic characteristics being summarized in appended claims.

We claim:

1. An injection syringe with device preventing reuse comprising:

a hollow syringe cylinder having a nozzle at one end adapted for connection to a hollow injecting needle, and being open at the other end;

a drive piston rod removably inserted into said open end of said cylinder for axial movement therein and having an inner end portion;

piston means sealingly and slidingly mounted within said cylinder between said one end and said drive piston rod for forcing fluid in said cylinder through said nozzle as said drive piston rod is urged inwardly towards said one end of said cylinder;

attachment means connecting said inner end portion of said drive piston rod with said piston means and providing relative bidirectional limited axial displacement between said piston means and said inner end portion of said drive piston rod;

an auxiliary element having sliding engaging means thereon for sliding engagement with said attachment means and with said piston means so that said auxiliary element is displaced axially with respect to said attachment means in a single direction by said bidirectional limited axial displacement produced by reciprocating axial movement of said drive piston rod; and means for preventing further use of the syringe after predetermined axial displacement of said auxiliary element.

2. An injection syringe as claimed in claim 1 wherein:

said piston means has an inner face facing said one end of said cylinder;

said attachment means comprises a hollow cavity within said piston means, a substantially radially extending end element on said inner end portion of said drive piston rod disposed within said cavity having an axial dimension smaller than that of said cavity to facilitate said bidirectional limited axial displacement between said piston means and said inner end portion of said drive piston rod;

first duct means extend through said inner end portion of said drive piston rod and through said end element communicating with said cavity;

second duct means extends through said piston means and the inner face thereof communicating with cavity with the hollow interior of said cylinder between said piston means and said one end of said cylinder;

vent passage means is provided communicating with said first duct means;

said auxiliary element comprises a pin member disposed partly in said first duct means and partly in said second duct means, and a groove in the outer surface of said pin member extending substantially axially a predetermined part of the length thereof; and said sliding engaging means comprises a toothed configuration on the outer surface of said pin member facilitating movement of said pin member through said inner end of said drive piston rod and said piston means in a single direction only, so that said pin member moves at least a distance sufficient for a part of said groove to extend through said inner face of said piston means to communicate the hollow interior of said cylinder between said piston means and said one end of said cylinder with said duct means and said vent means for preventing further use of the syringe.

3. An injection syringe as claimed in claim 2 wherein:

said toothed configuration comprises a plurality of truncated cones disposed relatively axially with respect to each other with the smaller bases thereof forward of the larger bases in the direction of said one end of said cylinder.

4. An injection syringe as claimed in claim 4 wherein:

each truncated cone has a height between the bases thereof substantially corresponding to said limited axial displacement between said piston means and said inner end portion of said drive piston rod.

5. An injection syringe as claimed in claim 2 and further comprising:

an auxiliary piston means slidingly and sealing mounted in said syringe cylinder between said piston means and said one end of said cylinder;

a rear face on said auxiliary piston means cooperatively engaging said inner face on said piston means prior to said predetermined axial displacement of said auxiliary element so that at least a partial vacuum is effected between said piston and auxiliary piston means and said auxiliary piston means adheres to said piston means during operation of the syringe until said auxiliary element is displaced an amount equal to said predetermined axial displacement relative to said piston means to cause release of said at least partial vacuum and disengagement of said faces whereby said auxiliary piston means is retained in said cylinder for preventing reuse of the syringe.

6. An injection syringe as claimed in claim 5 and further comprising:

a cavity in said auxiliary piston extending inwardly thereof from said rear face.

7. An injection syringe as claimed in claim 2 wherein:

said inner end portion on said drive piston rod comprises a radially enlarged end; and said substantially radially extending end element comprises a resilient end cap at least partially enclosing said enlarged end for being retained thereon.

8. An injection syringe as claimed in claim 1 and further comprising:

an inner face on said piston means facing said one end of said cylinder;

an auxiliary piston means slidingly and sealing mounted in said syringe cylinder between said piston means and said one end of said cylinder;

a rear face on said auxiliary piston means cooperatively engaging said inner face on said piston means prior to said predetermined axial displacement of said auxiliary element so that at least a partial vacuum is effected between said piston and auxiliary piston means and auxiliary piston means adheres to said piston means during operation of the syringe until said auxiliary element is displaced an amount equal to said predetermined axial displacement relative to said piston means to cause release of said at least partial vacuum and disengagement of said faces whereby said auxiliary piston means is retained in said cylinder for preventing reuse of the syringe.

9. An injection syringe as claimed in claim 8 and further comprising:

a cavity in said auxiliary piston extending inwardly thereof from said rear face.

* * * * *